(12) United States Patent
Hessefort et al.

(10) Patent No.: US 6,569,413 B1
(45) Date of Patent: May 27, 2003

(54) HAIR FIXATIVE COMPOSITION CONTAINING AN ANIONIC POLYMER

(75) Inventors: Yin Z. Hessefort, Naperville, IL (US); Douglas E. Betts, Warrenville, IL (US); Wayne M. Carlson, Batavia, IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

(21) Appl. No.: 09/833,364

(22) Filed: Apr. 12, 2001

(51) Int. Cl.$^7$ .............................. A61K 7/11; A61K 7/09; A61K 7/00
(52) U.S. Cl. ................. 424/70.11; 424/45; 424/47; 424/70.1; 424/70.16; 424/70.2; 424/70.4; 424/70.5
(58) Field of Search ............... 424/70.1, 70.11, 424/70.16, 45, 47, 70.2, 70.4, 70.5

(56) References Cited

U.S. PATENT DOCUMENTS

| | | | |
|---|---|---|---|
| 4,065,422 A | 12/1977 | Lundmark et al. ............. | 424/78 |
| 5,413,775 A | 5/1995 | Hatfield et al. ................ | 424/47 |
| 5,620,683 A | 4/1997 | Tong et al. ............... | 424/70.11 |
| 6,497,891 B2 * | 12/2002 | Bara ........................... | 424/401 |

FOREIGN PATENT DOCUMENTS

| | | |
|---|---|---|
| EP | 197 649 | 10/1986 |
| EP | 522 756 | 1/1993 |
| WO | 9221316 | * 12/1992 |

OTHER PUBLICATIONS

Ehlert et al. (DN 126:122299, abstract of DE 19523596, 1997).*

* cited by examiner

*Primary Examiner*—Sabiha Qazi
(74) *Attorney, Agent, or Firm*—Michael B. Martin; Thomas M. Breininger

(57) ABSTRACT

A cosmetically acceptable hair fixative composition comprising from about 0.1 to about 10 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic or nonionic monomers and a method of fixing hair are disclosed.

11 Claims, No Drawings

HAIR FIXATIVE COMPOSITION CONTAINING AN ANIONIC POLYMER

TECHNICAL FIELD

This invention relates to compositions and methods for treating hair. More particularly, this invention concerns a cosmetically acceptable hair fixative composition containing an anionic polymer and a method of using the composition for setting hair.

BACKGROUND OF THE INVENTION

Natural hair tends to return to its initial shape or position so it does not hold a set well. Hair styling and fixative products help build the interactive forces between hair fibers, which give adherence to the adjacent hairs so they can keep a particular shape or configuration as the polymer dries. In the past, hairsprays have dominated the styling aid market because of easy use, good styling and simple application. Pump hair sprays, hydrocarbon aerosols and carbon dioxide aerosols are three major types of sprays. However, hairsprays have largely used propellants and alcohol as their major components which are considered Volatile Organic Compounds (VOC).

Since government regulations are driving down permissible levels of VOC, the industry has reduced the VOC of their products. In most cases, this results in an increase in water content of the formula. But the increase in water content creates many problems such as resin solubility, increased viscosity, loss of holding power, increased initial curl droop and tackiness. In addition, increasing the water content of hair spray can also cause can corrosion and solvent/propellant incompatibility in aerosol formulations. Therefore, non-aerosol and water-based styling aid products such as styling gel, glaze, spray foam, styling cream and waxes, and styling lotion have been gradually replacing hairsprays.

High molecular weight polymers have been used as hair fixatives since 1940 and they have played the key role of holding the hair in place during the styling process and in the fixing step. Over the years, most of the hair fixative polymers were designed to be soluble in alcohol or propellants, and usually these polymers have poor solubility in water. As a result, their performance as a hair fixative is affected when water is incorporated into the formulation. Cationic polymers such as polyquatemium-11 and polyquatemium-4 are excellent film-forming polymers, but their high substantivities make them difficult to wash out. Consequently, anionic polymers are most frequently used.

However, because of their high solubility in water, anionic hair fixative polymers are also considered hygroscopic materials that often show poor hair setting properties in high humidity environments. It is thus an object of this invention to develop polymers that have a better balance between the conflicting requirements of water-indifference (good curl retention at high humidity) and water-sensitivity (rapid and complete removal from the hair when rinsed with water).

SUMMARY OF THE INVENTION

In its principal aspect, this invention is directed to a cosmetically acceptable hair fixative composition comprising from about 0.1 to about 10 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic or nonionic monomers.

In another aspect, this invention is directed to a method of setting hair comprising a) applying to the hair an effective setting amount of a cosmetically acceptable hair fixative composition comprising from about 0.1 to about 10 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic or nonionic monomers; and b) placing the hair in the desired configuration.

An advantage of this invention is that the anionic polymer performs well under high humidity and is easily removed by water.

Another advantage is that the anionic polymer has excellent compatibility with an anionic thickening system.

Another advantage is that the anionic polymer gives a silky feeling after the hair is dried.

DETAILED DESCRIPTION OF THE INVENTION

Definitions of Terms

"Anionic monomer" means a monomer as defined herein which possesses a net negative charge above a certain pH value. Representative anionic monomers include base addition salts of acrylic acid, methacrylic acid, itaconic acid, 2-acrylamido-2-methyl-1-propanesulfonic acid, sulfopropyl acrylate or methacrylate or other water-soluble forms of these or other polymerizable carboxylic or sulfonic acids, sulphomethylated acrylamide, allyl sulphonate, styrene sulfonic acid, sodium vinyl sulphonate, and the like. Preferred anionic monomers are acrylic acid and 2-acrylamido-2-methyl-1-propanesulfonic acid.

"Base addition salt" means the salt resulting from reaction of a carboyxlic acid (—$CO_2H$) group with a suitable base such as the hydroxide, carbonate, or bicarbonate of a metal cation or tetraalkylammonium cation, or with ammonia, or an organic primary, secondary, or tertiary amine of sufficient basicity to form a salt with the carboxylic acid group. Representative alkali or alkaline earth metal salts include sodium, lithium, potassium, calcium, magnesium, and the like. Representative organic amines useful for the formation of base addition salts include, ethylamine, diethylamine, ethylenediamine, ethanolamine, diethanolamine, piperazine, and the like. Preferred base addition salts include the sodium and ammonium salts.

"IV" stands for intrinsic viscosity, which is RSV extrapolated to the limit of infinite dilution, infinite dilution being when the concentration of polymer is equal to zero.

"Monomer" means a polymerizable allylic, vinylic or acrylic compound. The monomer may be anionic, cationic or nonionic. Vinyl monomers are preferred, acrylic monomers are more preferred.

"Nonionic monomer" means a monomer as defined herein which is electrically neutral. Representative non-ionic, water-soluble monomers include acrylamide, methacrylamide, N,N-dimethylacrylamide, N,N-diethylacrylamide, N-isopropylacrylamide, N-vinylformamide, N-vinylmethylacetamide, N-vinyl pyrrolidone, hydroxyethyl methacrylate, hydroxyethyl acrylate, hydroxypropyl acrylate, hydroxypropyl methacrylate, N-t-butylacrylamide, N-methylolacrylamide, and the like.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in *"Principles of Polymer Chemistry"*, Cornell University Press, Ithaca, N.Y., © 1953, Chapter VII, *"Determination of Molecular Weights"*, pp. 266–316. The RSV is measured at a given polymer concentration and temperature and calculated as follows:

$$RSV = \frac{[(\eta/\eta_o) - 1]}{c}$$

$\eta$ = viscosity of polymer solution $\eta_o$ = viscosity of solvent at the same temperature $c$ = concentration of polymer in solution.

The units of concentration "c" are (grams/100 ml or g/deciliter). Therefore, the units of RSV are dL/g. In this patent application, a 1.0 molar sodium nitrate solution is used for measuring RSV, unless specified. The polymer concentration in this solvent is 0.045 g/dL. The RSV is measured at 30° C. The viscosities $\eta$ and $\eta_o$ are measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dL/g. When two polymer homologs within a series have similar RSV's that is an indication that they have similar molecular weights.

"Solution polymer" means a water soluble anionic polymer as described herein that is prepared by solution polymerization. To conduct a solution polymerization of water soluble monomers, the desired monomers are dissolved in water, generally at concentrations between 5 and 40%, along with any buffers, acid or caustic, chelants and chain transfer agents. The solution is purged with nitrogen and heated to the polymerization temperature. After the polymerization temperature is reached, one or more water soluble initiators is added. These initiators may be either of the azo type or of the redox type. Then, depending on the desired polymer characteristics, the temperature is either allowed to rise uncontrolled (adiabatic) or is controlled with cooling to remove the heat generated (isothermal). After the polymerization is complete, the solution of polymer can be removed from the reaction vessel, transferred to storage and characterized.

Preferred Embodiments

In a preferred aspect of this invention, the anionic or nonionic monomers are selected from the group consisting of acrylic acid, methacrylic acid, acrylamide, methacrylamide and styrene sulfonic acid.

In another preferred aspect, the anionic polymer has a molecular weight of from about 20,000 to about 5,000,000.

In another preferred aspect, the anionic polymer is methacrylic acid/2-acrylamido-2-methyl-1-propanesulfonic acid sodium salt copolymer or acrylamide/2-acrylamido-2-methyl-1-propanesulfonic acid sodium salt copolymer.

The anionic polymers of this invention are used as compositions for treating hair by incorporating them in a cosmetically acceptable medium in amounts of from about 0.1 to about 10 percent, preferably from about 0.5 to about 5 percent by weight, based on polymer solids.

These compositions can be presented in various forms including hair spray, styling gel, styling glaze, spray foam, styling cream, styling wax, styling lotion, liquid foam and mousse. They can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerins, ethylene glycol and propylene glycol, and glycol ethers, such as mono-, di- and tri-ethylene glycol monoalkyl ethers, for example ethylene glycol monomethyl ether, ethylene glycol monomethyl ether and diethylene glycol monomethyl ether, used singly or in a mixture. These solvents can be present in proportions of up to as much as 99.5 percent by weight, relative to the weight of the total composition.

The compositions of this invention can also contain any other ingredient normally used in cosmetics, such as perfumes, dyestuffs which can serve to color the composition itself or the fibres of the hair, preservatives, sequestering agents, thickeners, silicones, softeners, foam synergistic agents, foam stabilizers, sun filters, peptising agents and also anionic, non-ionic, cationic or amphoteric surface-active agents or mixtures thereof.

The hair fixative composition of this invention is applied to wet or dry hair by spraying or by rubbing onto the hair manually. The treated hair is then mechanically fixed in the desired configuration using, for example, any of a variety of rollers or curlers. In the case of application to wet hair, the hair is then dried using ambient air, electric or hot air drying using, for example, a blow dryer. The hair is then combed to provide the desired hairstyle.

In another preferred aspect of this invention, the hair fixative composition is selected from the group consisting of gels, glazes and creams.

A hair styling gel is firm gel that thins upon application of shear such that it spreads very thin when applied to hair. Hair styling gels are typically applied by manually rubbing the gel onto wet or damp hair. The hair is then placed in the desired configuration, for example by wrapping the hair tightly around curlers or a finger and set by drying as described above. For a general treatise of hair styling and setting, see C. Zviak, *The Science of Hair Care*, 150–178 (1986).

Hair styling glazes are easy to spread, clear flowable gels that are particularly useful for the wet look or blow dry styling methods.

Hair styling creams are easy to spread, flowable lotions.

In addition to the anionic polymer and water and/or alcohol, the hair styling gel or glaze contains about 0.05 to about 15 percent by weight of a thickener. The thickener should be compatible with the anionic polymer and should not adversely affect the stability or efficacy of the hair styling gel. Representative thickeners include polyacrylic acid, polyacrylic acid crosslinked with allyl ethers of pentaerythrol or allyl ethers of sucrose (available from BF Goodrich, Brecksville, Ohio under the tradename Carbopol®), sodium acrylates copolymer (available from Ciba Specialty Chemicals Corporation, High Point, N.C. under the tradename Salcare®), xanthan gums, sodium alginates, gum arabic and cellulose derivatives. It is also possible to achieve thickening by means of a mixture of polyethylene glycol stearates or distearates or by means of a mixture of a phosphoric acid ester and an amide.

Other optional ingredients also can be incorporated into the hair styling gel or glaze. The identity of the optional ingredients is not limited as long as the optional ingredients do not adversely affect the aesthetics or efficacy of the hair styling gel. Such optional ingredients are well known to those skilled in the art and include emulsifiers such as anionic or nonionic surfactants; preservatives such as benzyl alcohol, methyl paraben, propyl paraben, or imidazolidinylurea; cationic conditioners such as cetyl trimethyl ammonium chloride, methyldibromoglutaronitrile (available from ONDEO Nalco, Naperville, Ill. under the tradename Merguard®), stearyl dimethyl benzyl ammonium chloride, and di(partially hydrogenated tallow) dimethyl ammonium chloride; coloring agents such as any of the FD&C or D&C dyes; perfume oils; and chelating agents such as ethylenediaminetetraacetic acid.

The hair fixative composition of this invention may also contain conventional hair care adjuvants including plasticizers such as glycols, phthalate esters and glycerine, silicones, emollients, lubricants, and penetrants such as various lanolin compounds, protein hydrolysates and other protein derivatives, ethylene adducts and polyoxyethylene cholesterol.

The hair fixative composition of this invention can also contain electrolytes, such as aluminum chlorhydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

The hair fixative composition of this invention may also contain one or more additional hair fixative polymers. When present, the additional hair fixative polymers are present in a total amount of from about 0.25 to about 5 percent by weight. Representative hair fixative polymers compatible with anionic and nonionic hair fixative polymers include acrylic/acrylate copolymer, allyl stearate/vinyl acetate (VA) copolymer, AMP acrylate/diacetoneacrylamide copolymer, butyl ester of ethylene/maleic anhydride (MA) copolymer, butyl ester of PVM/MA copolymer, isopropyl ester of PVM/MA copolymer, octylacrylamide/acrylate/butylaminoethyl methacrylate copolymer, phthalic anhydride/glycerin/glycidyl decanoate copolymer, polybutylene terephthalate, polyethylacrylate, polyethylene, polyvinyl acetate, polyvinyl butyral, polyvinyl methyl ether, polyvinylprrolidinone (PVP), PVP/VA, PVP/dimethylaminoethylmethacrylate copolymer, PVP/eicosene copolymer, PVP/ethyl methacrylate/methacrylic acid copolymer, PVP/hexadecene copolymer, PVP/VA/itaconic acid copolymer, sodium acrylate/vinyl alcohol copolymer, starch diethylaminoethyl ether, stearylvinyl ether/maleic anhydride copolymer, VA/crotonate copolymer, VA/crotonic acid copolymer, VA/crotonic acid/methacryloxybenzophenone-1 copolymer, VA/crotonic acid/vinyl neodecanoate copolymer, and the like.

The hair styling gels of the present invention are prepared by dissolving the anionic polymer in water or a water/alcohol mixture, with heating if necessary. An aqueous solution of the viscosity enhancer and any optional ingredients are then added and the mixture is stirred to provide the gel or glaze.

When the hair fixative composition is in the form of a hair spray or mousse, it additionally contains up to 50 weight percent of one or more propellants. Typical propellants include ethers, compressed gases, halogenated hydrocarbons and hydrocarbons including, dimethyl ether, carbon dioxide, nitrogen, nitrous oxide and volatile hydrocarbons, such as butane, isobutane, propane, and the like.

The foregoing may be better understood by reference to the following examples, which are presented for purposes of illustration and are not intended to limit the scope of this invention.

EXAMPLE 1

Preparation of a Representative Acrylic Acid/2-acrylamido-2-methyl-1-propanesulfonic Acid Sodium Salt Copolymer To a 1.5-liter resin reactor equipped with stirrer, temperature controller, and water cooled condenser is added 1690.19 g of deionized water, 229.01 g of a 58% solution of the sodium salt of 2-acrylamido-2-methyl-1-propanesulfonic acid (AMPS), 80.00 g of acrylic acid and 0.20 g of EDTA. The resulting solution is sparged with 1 L/min. of nitrogen, heated to 72° C. and 0.10 g of sodium bisulfite and 0.50 g of 2,2' azobis(N,N'2-amidinopropane) dihydrochloride (V-50, Wako Chemicals, Richmond, Va., USA) are added. Polymerization begins within 5 minutes and after 10 minutes, the solution becomes viscous and the temperature of the reaction rises to 80° C. The reaction is continued for a total of 16 hours at 78–82° C. The resulting 10% polymer solution has a Brookfield viscosity of 1000 cps at 25° C. and contains a 60/40 w/w copolymer of acrylic acid/AMPS with an intrinsic viscosity of 2.8 dL/g in 1.0 molar $NaNO_3$.

The properties of representative acrylic acid/2-acrylamido-2-methyl-1-propanesulfonic acid sodium salt (AA/AMPS) copolymers are summarized in Table 1.

TABLE 1

| Properties of Representative AA/AMPS Copolymers | | | | | |
|---|---|---|---|---|---|
| Anionic Polymer | AA/AMPS (wt/wt) | AA/AMPS (mol/mol) | RSV @ 1.0% (dL/g) | IV (dL/g) | VISC (cps) |
| 1 | 60/40 | 80/20 | 3.0 | 2.8 | 1000 |
| 2 | 40/60 | 66/34 |  | 2.8 | 1000 |
| 3 | 60/40 | 81/19 |  | 2.0 | 487.5 |
| 4 | 90/10 | 90/10 |  | 3.6 | 7040 |
| 5 | 60/40 | 81/19 |  | 8.0 | 63300 |
| 6 | 60/40 | 81/19 |  | 1.9 | 19250 |

EXAMPLE 2

Preparation of a Representative Methacrylic Acid/2-acrylamido-2-methyl-1-propanesulfonic Acid Copolymer To a 1.5-liter resin reactor equipped with stirrer, temperature controller, and water cooled condenser is added 939.21 g of deionized water, 191.92 g of a 58% solution of the sodium salt of 2-acrylamido-2-methyl-1-propanesulfonic acid (AMPS), 99.50 g of methacrylic acid, 92.00 g of a 50% solution of sodium hydroxide (to adjust the reaction mixture to pH=7.0) and 0.20 g of EDTA. The resulting solution is sparged with 1 L/min. of nitrogen, heated to 45° C. and 0.50 g of V-50 is added. Polymerization begins within 15 minutes and after 60 minutes, the solution becomes viscous and the temperature of the reaction rises to 50° C. The reaction is continued for 18 hours at 48–52° C. The reaction mixture is then heated to 80° C. and maintained at 78–82° C. for 24 hours. The resulting polymer solution has a Brookfield viscosity of 43200 cps at 25° C. and contains 15% of a 49/51 w/w (70/30 M/M) copolymer of methacrylic acid/AMPS with an intrinsic viscosity of 4.28 dL/gm in 1.0 molar $NaNO_3$.

The properties of representative methacrylic acid/2-acrylamido-2-methyl-1-propanesulfonic acid sodium salt (MAA/AMPS) copolymers are summarized in Table 2.

TABLE 2

Properties of Representative MAA/AMPS Copolymers

| Anionic Polymer | MAA/AMPS (wt/w) | MAA/AMPS (mol/mol) | RSV @ 1.0% (dL/g) | IV (dL/g) | VISC (cps) |
|---|---|---|---|---|---|
| 7 | 62.5/37.5 | 80/20 | 8.2 | 4.3 | 61300 |
| 8 | 79/21 | 90/10 | 5.4 | 3.1 | 24375 |
| 9 | 49/51 | 70/30 | 9.1 | 4.3 | 43200 |
| 10 | 38.4/61.6 | 60/40 | 6.8 | 3.6 | 32500 |
| 11 | 29.4/70.6 | 50/50 | 7.0 | 3.6 | 31750 |
| 12 | 29.4/70.6 | 50/50 | 5.1 | 3.1 | 15100 |
| 13 | 21.7/78.3 | 40/60 | 4.3 | 2.9 | 9420 |
| 14 | 15.3/84.7 | 30/70 | 3.8 | 2.5 | 6470 |
| 15 | 9.4/90.6 | 20/80 | 3.9 | 2.5 | 8150 |

EXAMPLE 3

Preparation of a Representative Acrylamide/2-acrylamido-2-methyl-1-propanesulfonic Acid Sodium Salt Copolymer Into a 1.5-liter resin reactor equipped with stirrer, temperature controller, and water cooled condenser is added 225.07 g of 2-acrylamido-2-methyl-1-propanesulfonic acid sodium salt (Na-AMPS) (58% solids), 191.61 g of acrylamide (49.3% solids), 1080.70 g of deionized water, 0.50 g of a 40% solution of EDTA and 0.50 g of sodium hypophosphite. Once the monomer solution has been added, the beaker is rinsed with 600 g of deionized water and the rinse is added to the reactor. The reaction mixture is stirred and heated to 45° C. Once at 45° C., 1.1 3 g of a 10% wt solution of 2,2'-azobis[2-(2-imidazolin-2-yl)propane] dihydrochloride (VA-044, Wako Chemicals USA, Inc., Richmond, Va.) initiator (500 ppm based on monomer) is added and the reaction mixture is purged with nitrogen at approximately 1 L/min. After several minutes the reaction mixture becomes viscous. After approximately eight hours, the reaction mixture is cooled to room temperature and the contents are discharged. The polymer has an IV of about 2.5 dL/g and a Brookfield viscosity of about 5700 cps (15% polymer solution).

EXAMPLE 4

Styling Gel Formulation

A representative hair styling gel formulation is shown in Table 3.

TABLE 3

Representative Hair Styling Gel Formulation

| Component | Weight Percent |
|---|---|
| Water | 96.11 |
| Anionic Polymer | 1.0% (solid) |
| Carbomer resin | 0.5 |
| Propylene Glycol | 1.0 |
| Benzophenon-4 | 0.1 |

TABLE 3-continued

Representative Hair Styling Gel Formulation

| Component | Weight Percent |
|---|---|
| Methylparaben | 0.5 |
| Propylparaben | 0.04 |
| Triethyanolamine(99%) | 0.5 |
| Oleth 20 | 0.2 |
| Disodium EDTA | 0.05 |

The gel is prepared by dispersing carbomer resin (Carbopol® 980, BF Goodrich, Brecksville, Ohio) in one/half of the total volume of water with stirring for three hours. A solution of methylparaben (Nipagin®, NIPA Inc., Wilmington, Del.) and propylparaben (Nipasol®, NIPA Inc., Wilmington, Del.) in propylene glycol is added to the carbomer dispersion, followed by Benzophenon-4 (ESCALOL® 577. ISP Van Dyk, Belleville, N.J.), Oleth 20 (Ameroxol® OE-20, Amerchol Corp., Edison, N.J.) and disodium EDTA (Versene®, Dow Chemical, Midland, Mich.). Triethanolamine is then added to form a gel. Finally, a solution of the anionic polymer in the remaining water is added slowly to the gel and the pH is adjusted to about 6.5 with citric acid or sodium hydroxide.

EXAMPLE 5

Representative Styling Gel Hair Styling Glaze Formulation

A representative hair styling glaze formulation is shown in Table 4.

TABLE 4

Representative Glaze Formulation

| Component | Weight Percent |
|---|---|
| Anionic Polymer | 1.0 |
| Water | 97.9 |
| Hydroxyethylcellulose | 0.7 |
| Alkylquat | 0.3 |
| preservatives | 0.1 |

The glaze is prepared by agitating a solution of hydroxyethylcellulose (Natrosol HHR, Hercules Inc., Wilmington, Del.) in one half of the volume of water with agitation for 4 hours. Alkylquat (Incroquot 26, Croda Inc., Parsippany, N.J.) is added to the solution followed by a solution of the anionic polymer in the remaining water. The pH of the glaze is adjusted to about 6.5 with citric acid or sodium hydroxide.

EXAMPLE 6

Representative Styling Cream Formulation

A representative hair styling cream formulation is shown in Table 5.

TABLE 5

Representative styling cream formulation

| Component | Weight Percent |
|---|---|
| Deionized Water | 96.67 |
| Sodium Acrylates copolymer/glycine | 1.21 (solid) |

TABLE 5-continued

Representative styling cream formulation

| Component | Weight Percent |
| --- | --- |
| soja/PPG-1, 50% Anionic polymer | 0.4 (solid) |
| Cyclomethicone | 1.56 |
| Methyldibromo Glutarolnitrile | 0.16 |

The styling cream is prepared by adding the sodium acrylates copolymer thickener (Salcare® AST, Ciba Specialty Chemicals, Highpoint, N.C.) to water (60% of the formulation) and mixing at 300 rpm until the mixture thickens and then for 30 minutes at 500 rpm. In a separate beaker, the anionic polymer is diluted with the remaining water and mixed for easier addition. Cyclomethicone (Dow Coming® 245 fluid, Dow Corning, Midland, Mich.), methyldibromo glutarolnitrile with 80% phenoxyethanol (Merguard® 1200, ONDEO Nalco, Naperville, Ill.), preservative and the anionic polymer solution are then added and the pH of the mixture is adjusted to about 7 with citric acid or NaOH.

EXAMPLE 7

Preparation of Hair Tresses for Testing

Six inch long, bleached, and hand made hair tresses are available from DeMeo Brothers Inc., New York, N.Y.).

The tresses are prepared for testing by cutting ⅛" width of hair from the pretabbed hair tress (0.4 g for each tress). The hair tress is wetted with water and then 0.3 g of sodium laureth sulfate is massaged onto the hair tress from top to bottom for 1 minute. The hair tress is then rinsed under 40±2° C. tap water for 1 minute. The washed hair tresses are soaked in deionized water overnight.

EXAMPLE 8

Curl Retention Using an Aqueous Anionic Polymer Solution

Clean hair tresses, prepared as in Example 7, are immersed in a 0.5 weight percent aqueous polymer solution for 2 minutes. The excess solution is squeezed from the tress with gloved fingers. Each tress is combed to detangle with the wide end of Sally Styling Combs, then the hair is rolled onto a roller (11/16" in diameter). The hair rolls are placed in a 50% relative humidity room overnight. The next day, the hair is unwound from each roller and the curled hair is placed in a 90% relative humidity chamber. The length of the curl (fall-out) is measured every 15 minutes for 2 hours and curl retention is calculated by the following equation:

Equation 1: Curl Retention Calculation $$\% \ Curl \ Retention = \frac{(L - Lt)}{(L - Lo)} \times 100$$

Where L=Length of hair tress fully extended
Lo=Length of hair tress at beginning of experiment
Lt=length of hair tress at time of measurement The results (average of 6 tests) for curl retention of a representative anionic polymer are shown in Table 6.

TABLE 6

Curl Retention Test for Aqueous Anionic Polymer Solution
Percent Curl Retention

| Time (min) | Control | Polymer 9 |
| --- | --- | --- |
| 15 | 70.3 | 98.8 |
| 30 | 54.1 | 96.3 |
| 45 | 47.5 | 93.0 |
| 60 | 45.0 | 92.2 |
| 75 | 43.8 | 89.8 |
| 90 | 41.8 | 88.5 |
| 105 | 41.0 | 87.7 |
| 120 | 40.6 | 87.7 |

The curl retention test results shown in Table 6 show that the anionic polymers of this invention have substantial holding power, even in a high humidity environment (87% curl retention after 2 hours at 90 percent relative humidity).

EXAMPLE 9

Curl Retention for Styling Gel Containing a Representative Anionic Polymer

To a 2 g washed hair tress is evenly applied 0.5 gram of the styling gel formulation of Example 4. The hair tress is dried using a hair dryer at 65° C. for 5 minutes. The hair is rolled onto a roller and the hair roller is placed in a 50% humidity room for 2 hours. The hair is then unrolled from the roller and the curl retention is measured as in Example 8. The results are summarized in Table 7.

TABLE 7

Curl Retention of Styling Gel containing Anionic Polymer
Percent Curl Retention

| Time (min) | Control | Polymer 9 |
| --- | --- | --- |
| 15 | 71.3 | 93.9 |
| 30 | 41.7 | 90.2 |
| 45 | 39.1 | 86.2 |
| 60 | 36.5 | 83.7 |
| 75 | 33.9 | 83.7 |
| 90 | 32.6 | 82.9 |
| 105 | 32.2 | 81.3 |
| 120 | 29.6 | 80.5 |

As shown in Table 7, a styling gel composition according to this invention has substantial holding power.

EXAMPLE 10

Curl Retention for Styling Glaze Containing a Representative Anionic Polymer

To a 2 g washed hair tress is evenly applied 0.5 g of the styling glaze formulation of Example 5. The hair tress is dried using a hair dryer at 65° C. for 5 minutes. The hair is rolled onto a roller and the hair roller is placed in a 50% humidity room for 2 hours. The hair is then unrolled from the roller and the curl retention is measured as in Example 6. The results are summarized in Table 7.

TABLE 8

Curl Retention of Styling Glaze containing Anionic Polymer
Percent Curl Retention

| Time (min) | Control | Polymer 9 |
|---|---|---|
| 15 | 70.5 | 96.2 |
| 30 | 61.5 | 88.7 |
| 45 | 58.9 | 86.2 |
| 60 | 58.3 | 82.8 |
| 75 | 57.0 | 79.9 |
| 90 | 53.8 | 79.5 |
| 105 | 52.5 | 77.8 |
| 120 | 51.3 | 77.4 |

As shown in Table 8, a hair styling glaze containing the anionic polymer of this invention exhibits also exhibits substantial curl retention.

EXAMPLE 11

Curl Memory for Styling Cream Containing a Representative Anionic Polymer

A 2 g, 6 inch washed hair tress is combed 10 times (Sally comb, large tooth part) to detangle, and 1 g of styling cream is applied to the hair tress. The hair tress is dried for 1.5 hours at room temperature at 30% relative humidity. A curling iron (Conair Instant Heat) at setting 20, 1 inch barrel is then used to curl each tress. After counting to 30, the curl is released and allowed to cool for five minutes at 50% relative humidity. The fall-out length is recorded after 5 and 30 minutes. The shorter the fall-out length of hair curl the better the curl memory. Duplicate hair tresses are tested. The results are summarized in Table 9.

TABLE 9

Curl memory Test of Styling Cream containing anionic polymer

| | Fall-Out Length (inches) | |
|---|---|---|
| Time (min) | Control (no polymer) | Anionic Polymer |
| 5 | 3.06 | 2.25 |
| 30 | 3.88 | 2.44 |

As shown in Table 9, a hair styling cream containing the anionic polymer of this invention exhibits high curl memory.

EXAMPLE 12

Wash off Panel Assessment

The ease of removal of the hair fixative composition of this invention from hair is evaluated using blind wash off panel testing. The test is subjective because the results reflect the opinions and perceptions of the panelists. The results do, however, provide an excellent way of determining how a consumer will perceive the properties of a product on the hair.

In this test, excess water is squeezed from a washed hair tress and 0.5 g of the styling gel of Example 4 is evenly apply to the hair. Each hair tress is dried using a hair dryer at 65° C. for 5 minutes and then placed in a 50 percent relative humidity room for 3 hours. The hair tresses are then soaked in 12% sodium laureth sulfate solution for 15 minutes, rinsed under deionized water for 1 minute and then soaked twice in deionized water for 10 minutes. The excess water is the squeezed from the hair tress. The hair tress is evaluated by holding the tress in one hand and using the other hand to touch the hair up and down to feel the slipperiness of the hair. The hair is then combed five times to remove all the tangles and the tress is combed twice with the fine end of the Sally comb to evaluate the ease of the combing. The slipperiness and ease of combing is rated on the following scale.

| Hair Slipperiness | Combing |
|---|---|
| 5 = Very slippery | 5 = Very easy |
| 4 = Slippery | 4 = Easy |
| 3 = Moderately slippery | 3 = Moderately easy |
| 2 = Slightly slippery | 2 = Slightly easy |
| 1 = Not slippery | 1 = Not easy |

The results are summarized in Table 10.

TABLE 10

Panel Testing of a Styling Gel containing a Representative Anionic Polymer for Hair Slipperiness and Ease of Combing

| Polymer | Slippery Feel | Combing |
|---|---|---|
| None | 2 | 1.5 |
| Polymer 9 | 2.7 | 2.4 |

The results of the panel test indicate that the hair fixative compositions of this invention are easily washed from the hair, and further impart a feeling of wet slip, silkiness and enhanced dry combability to the hair.

EXAMPLE 13

Compatibility of Representative Anionic Polymers with Additional Hair Fixatives

The anionic polymer of this invention is compatible with most commonly used hair fixatives.

The following tables show styling aid formulations having a combination of anionic polymer with poly (vinylpyrrolidone) and poly(vinylpyrrolidone/vinyl acetate) copolymer. The formulations described in Tables 11 and 12 are prepared as described in Examples 4 and 6, respectively. The styling gel and cream show no separation after 2 weeks.

TABLE 11

Representative Hair Styling Gel Formulation containing PVP and anionic polymer

| Component | Weight Percent |
|---|---|
| Deionized Water | 96.11 |
| Carbomer 980 Resin (BF Goodrich) | 0.5 |
| Poly(vinylpyrrolidone) | 0.25 (solid) |
| Polymer 9 | 0.75 (solid) |
| Propylene Glycol | 1.0 |
| Benzophenon-4 | 0.1 |
| Methylparaben | 0.5 |
| Propylparaben | 0.04 |
| Triethyanolamine(99%) | 0.5 |
| Oleth 20 | 0.2 |
| Disodium EDTA | 0.05 |

TABLE 12

Representative Hair Styling Cream containing PVP/VA and anionic polymer

| Component | Weight Percent |
| --- | --- |
| Deionized Water | 96.47 |
| Sodium Acrylates copolymer/glycine soja/PPG-1, 50% | 1.21 (active) |
| Poly(vinylpyrrolidone/vinyl acetate) | 0.2 (solid) |
| Polymer 9 | 0.4 (solid) |
| Cyclomethicone | 1.56 |
| Methyldibromo Glutarolnitrile | 0.16 |

Various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A cosmetically acceptable hair fixative composition comprising from about 0.1 to about 10 weight percent, based on polymer solids, of an anionic polymer, wherein the anionic polymer is composed of from about 10 to about 80 mole percent of 2-acrylamido-2-methyl-1-propanesulfonic acid or a base addition salt thereof and from about 90 to about 20 mole percent of one or more anionic monomers.

2. The hair fixative composition of claim 1 wherein the anionic monomers are selected from the group consisting of acrylic acid, methacrylic acid and styrene sulfonic acid.

3. The hair fixative composition of claim 1 wherein the anionic polymer has a molecular weight of from about 20,000 to about 5,000,000 g/mol.

4. The hair fixative composition of claim 1 wherein the anionic polymer is methacrylic acid/2-acrylamido-2-methyl-1-propanesulfonic acid sodium salt copolymer.

5. The hair fixative composition of claim 1 wherein the hair fixative composition is selected from the group consisting of hair spray, styling gel, styling glaze, spray foam, styling cream, styling wax, styling lotion, liquid foam and mousse.

6. The hair fixative composition of claim 5 comprising from about 0.5 to about 5 weight percent, based on polymer solids, of the anionic polymer.

7. The hair fixative composition of claim 6 wherein the anionic polymer is methacrylic acid/2-acrylamido-2-methyl-1-propanesulfonic acid sodium salt copolymer.

8. The hair fixative composition of claim 7 selected from the group consisting of gels, glazes and creams.

9. The hair fixative composition of claim 1 further comprising one or more additional hair fixative polymers.

10. A method of setting hair comprising a) applying to the hair an effective setting amount of the hair fixative composition of claim 1; and b) placing the hair in the desired configuration.

11. The method of claim 9 wherein the hair is wet or damp.

* * * * *